US 6,739,450 B2

(12) United States Patent
Roshdy et al.

(10) Patent No.: US 6,739,450 B2
(45) Date of Patent: May 25, 2004

(54) TWO-TIERED MULTISTRAND SUTURE FOLDER

(75) Inventors: Constance E. Roshdy, Mount Bethel, PA (US); Elizabeth Porras, South Round Brook, NJ (US)

(73) Assignee: Ethicon, Inc., Somerville, NJ (US)

( * ) Notice: Subject to any disclaimer, the term of this patent is extended or adjusted under 35 U.S.C. 154(b) by 229 days.

(21) Appl. No.: 10/105,063

(22) Filed: Mar. 22, 2002

(65) Prior Publication Data

US 2003/0178325 A1 Sep. 25, 2003

(51) Int. Cl.⁷ .............................................. A61B 17/06
(52) U.S. Cl. ...................... 206/63.3; 206/227; 206/380
(58) Field of Search ............................... 206/63.3, 227, 206/380, 381, 382

(56) References Cited

U.S. PATENT DOCUMENTS

| | | |
|---|---|---|
| 4,034,850 A | 7/1977 | Mandel et al. |
| 4,063,638 A | 12/1977 | Marwood |
| 4,120,395 A | 10/1978 | Mandel et al. |
| 4,391,365 A | 7/1983 | Batchelor |
| 4,699,271 A | 10/1987 | Lincoln et al. |
| 5,386,912 A | 2/1995 | Holzwarth et al. |
| 5,562,211 A | 10/1996 | Simons et al. |
| 5,582,288 A * | 12/1996 | Zatarga ..................... 206/63.3 |
| 5,601,185 A | 2/1997 | Behring et al. |
| 5,769,214 A | 6/1998 | Zatarga |
| 5,871,089 A | 2/1999 | Odermatt |
| 6,029,806 A | 2/2000 | Cerwin et al. |
| 6,260,699 B1 | 7/2001 | Kaplan et al. |

FOREIGN PATENT DOCUMENTS

| | | | |
|---|---|---|---|
| EP | 0697196 | 2/1996 | |
| EP | 1346693 A1 * | 9/2003 | ........... A61B/17/06 |
| GB | 2148232 A * | 5/1985 | ........... A61B/17/04 |
| WO | 9305714 | 4/1993 | |

* cited by examiner

Primary Examiner—Jila M. Mohandesi (57) ABSTRACT

A suture package for multiple double armed sutures has a base panel with a multi-compartment pocket disposed at a bottom portion thereof. A needle park adhered to the base panel holds a first group of needle pairs with the associated sutures extending down into compartments of the pocket. A divider panel divides the pocket structure in half and supports a second needle park for holding a second plurality of needle pairs. The needle parks have a serrated top edge and angled slits that hold the needles such that they have a reduced lateral profile to allow the package to have a manipulable width while holding multiple sutures. Pledgets on the sutures park besides the needles in valleys of the serrated edge. In order to prevent the second panel from compressing the sutures when the package is folded, the fold lines of the base panel and the second panel are offset and the top portion of the second panel is slidably attached to the base panel by tabs and slots.

23 Claims, 6 Drawing Sheets

TWO-TIERED MULTISTRAND SUTURE FOLDER

FIELD OF THE INVENTION

The present invention relates to packages for sutures, and, more particularly, to packages for multiple double-armed sutures wherein each suture may include a pledget centered thereon and is removable from the package without tangling or knotting.

BACKGROUND OF THE INVENTION

Double-armed sutures, i.e., a surgical suture with a needle at each end, are well known and commonly used, e.g., in cardiovalve replacement surgery. This type of suture is optionally manufactured with a pre-centered pledget, i.e., a cushioning pad that prevents the suture from cutting into sutured tissue. Such sutures are frequently packaged in sets to supply an adequate number to advance the surgery without requiring opening and handling multiple packages. The sutures are typically arranged in the package with the needle ends of each suture grouped together such that the two ends of each suture can be identified. The sutures are provided in at least two different colors to aid in visually identifying each suture. It is preferable for the suture package to facilitate dispensing each suture by grasping one or both of the associated needles with a needle holder.

During surgery, a rhythm is developed between the scrub nurse and the surgeon in passing the sutures to the surgeon. If a suture becomes tangled upon removal from the package, this rhythm is interrupted and lengthens the surgery, which poses a danger to the patient. Accordingly, it remains an objective in this field to provide suture packaging that minimizes the chances of suture tangling.

Various suture winding and packaging schemes are now known for facilitating suture storage and dispensing from a package holding a plurality of sutures. For example, U.S. Pat. No. 6,029,806 entitled "PACKAGE FOR DOUBLE ARMED SUTURES" and owned by the present Assignee is incorporated by reference herein for its teachings concerning the storage of multiple sutures in a suture package having a plurality of pockets with plural compartments stacked in the Z direction.

Surgeons variously prefer to handle either a single needle holder, which is sequentially used to grasp a first needle of the suture then the second needle, or a pair of needle holders, which are used for simultaneously grasping both needles. It is desirable for each needle to be presented in the package with adequate space around it for the scrub nurse to readily grasp each needle individually with a needle holder. Spatial separation of the needles must not disturb their functional grouping, i.e., it must be apparent which two needles are connected to the same suture. It is also desirable for the sutures to be visually distinct. Furthermore, spatial separation of the needles and other beneficial features cannot be allowed to appreciably enlarge the needle package to the degree that it becomes unwieldy or that it cannot be accommodated in the standard storage devices present in the operating room and supply cabinets.

Owing to the conflicting objectives of storing greater numbers of sutures in smaller packaging, instances of compression and bending of the sutures and pledgets occur. With respect to pledgets, it is beneficial that they be delivered to the surgical site as flat as possible so that the contact surface area thereof relative to the sutured tissue is maximized to realize maximum force distribution. It is beneficial if the sutures are free of folds and flats along their entire length.

Because there are a variety of suture packages made by various manufacturers, in addition to a great variety of different kinds of sutures, it would be beneficial to have a convenient and effective means of communicating information concerning the sutures and/or the suture package to the surgeon and/or the scrub nurse at the time of suture use. Suture packages having identification and/or use information printed on sleeves that are separated from the package when it is opened require the printed material to be separately positioned on a crowded Mayo stand, e.g., juxtaposed next to the portion of the package holding the sutures. Accordingly, it would be beneficial for identification and/or use information to be printed on a part of the suture package that remains attached to the portion holding the needles.

It is therefore an object of the present invention to provide a new and improved package for multiple double-armed sutures that provides greater suture discrimination and ease of arming while preventing tangling of the sutures and, on sutures so supplied, keeping a pledget protected and centered on the suture upon withdrawal from the package. It is also desirable to have a package that is easy to handle, yet is capable of holding multiple sutures. Another object of the invention is to provide a package that applies minimal compression pressure to the sutures, such that the sutures are not flattened or folded, are loose within the package, and are therefore easy to remove. Yet another objective is to realize the foregoing objectives in a manner that is efficient and economical.

SUMMARY OF THE INVENTION

The limitations of known suture packages are addressed by the present invention which includes a suture package with a base panel and a first needle park attached to a front surface of the base panel for holding a first needle. The first needle is attached to a first suture and a pocket having a plurality of compartments is disposed on the front surface of the base panel. A first of the plurality of compartments receives the first suture. A second panel, smaller than the base panel is coupled to the base panel substantially parallel thereto with the first suture disposed between the second panel and the base panel. A second needle park is attached to a front surface of the second panel for holding a second needle, which is attached to a second suture. A second of the plurality of compartments receives the second suture.

BRIEF DESCRIPTION OF THE DRAWINGS

For a better understanding of the present invention, reference is made to the following detailed description of an exemplary embodiment considered in conjunction with the accompanying drawings, in which.

DETAILED DESCRIPTION OF THE INVENTION

Figure 1:
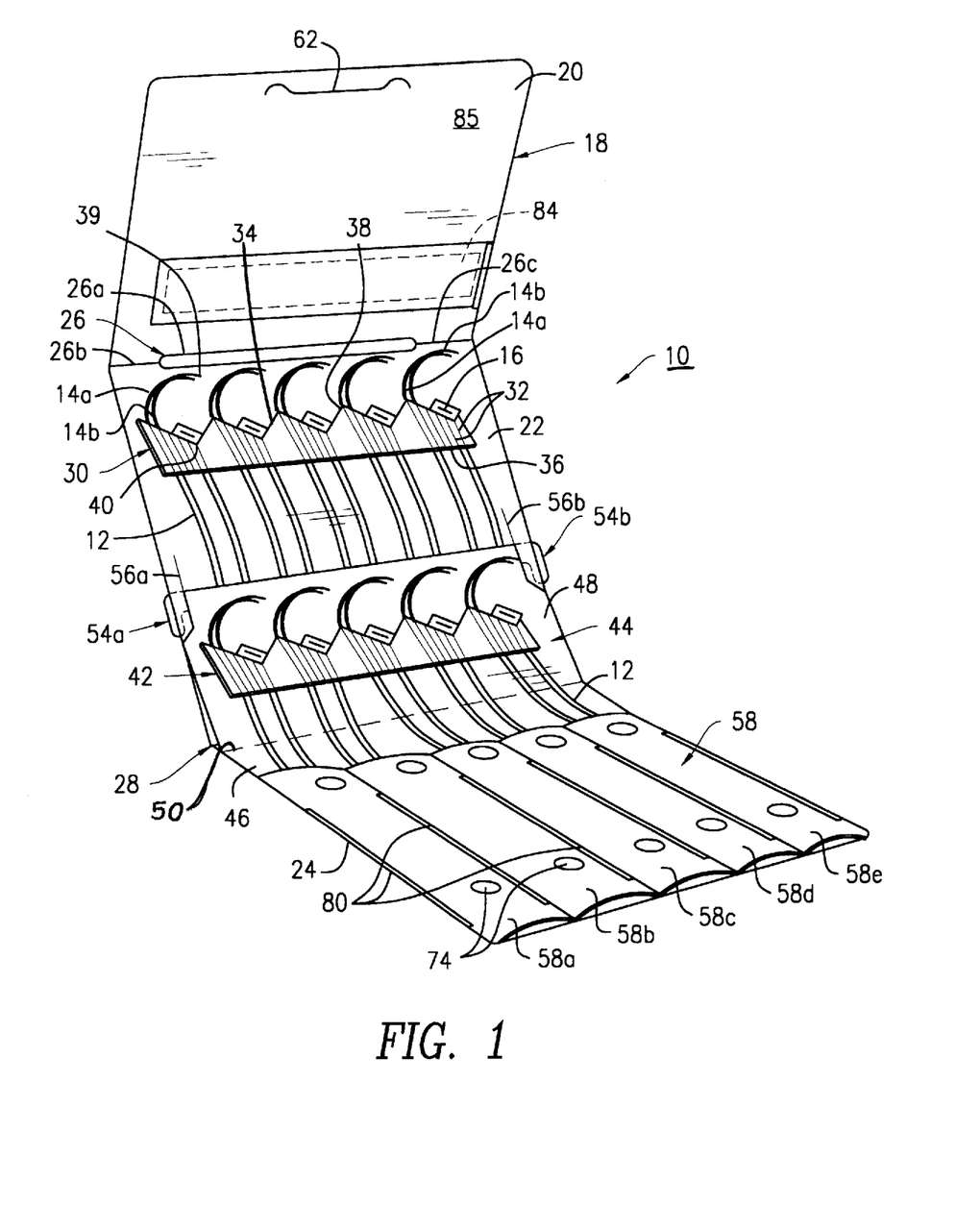
FIG. 1 is a perspective view of a suture package in accordance with an exemplary embodiment of the present invention.

FIG. 1 shows a suture package 10 designed for storing and dispensing sutures 12 of a particular length, e.g., 30 inches. It is possible for the package 10 to hold sutures 12 of different lengths. The sutures 12 have needles 14a, 14b, at the ends thereof and a pledget 16 disposed at the approximate middle. The suture package 10 has a main folder 18, which serves as a base panel upon which the suture package 10 is built. The main folder 18 (also shown in FIG. 4) has three subpanels 20, 22, 24 defined by gusseted fold lines 26 and 28, each of which has a central polygonal portion 26a, 28a disposed between two short straight folds 26b, 26c, 28b, 28c, respectively. The polygonal portions 26a, 28a cause the subpanels, 20, 22 and 22, 24 to be spaced one from another at the fold lines 26, 28 when the package 10 is folded, such spacing accommodating the sutures 12, needles 14a, 14b and pledgets 16 without undue compression. The middle subpanel 22 has a needle park 30 thereon with a plurality of slits 32 to receive a plurality of needles 14a, 14b. The slits 32 extend from an upper serrated edge 34 of the needle park 30 to a lower straight edge 36 thereof. The slits 32 are disposed at an angle relative to edge 36 and are laterally spaced such that needle sets 14a, 14b associated with each suture 12 are spaced one from another in adjacent slits 32. Preferably, the needles 14a, 14b are inserted in slits 32 proximate peaks 38 in the serrated edge 34. This arrangement permits the middle portion of the suture 12 where the pledget 16 is installed to be "parked" in a slit 32 adjacent to one of the associated needles, e.g., 14b. Preferably, the pledget 16 is parked in a valley 40 of the serrated edge 32. In this manner, the needles 14a, 14b of each suture 12 are spacially grouped but separated sufficiently to be grasped individually by a needle holder (not shown) The needles 14a, 14b are inserted into the needle park 30 proximate to the suture 12, i.e., where they are connected to the suture 12, e.g., by swaging. In this manner, each needle 14a, 14b may be grasped by a needle holder (not shown) at any point along the length of the needle 14a, 14b, e.g., at the approximate middle thereof. In addition, the pledget 16 is protected in the valley 40 of the needle park 30 adjacent to and below the associated needles 14a, 14b of the suture 12. The thickness of the needle park 30 shields the pledgets 16 from compression and/or folding. The needle park 30 is preferably made from foam or other elastomer and has sufficient slits 32 to accommodate several sutures 12 and associated needles 14a, 14b.

The geometry of the needle park 30 may be utilized to promote the compact storage of multiple needle pairs 14a, 14b in a given package width, thereby limiting the "foot print" of the package 10 and assuring ease of handling and storage in existing dispenser racks. More particularly, the needles 14a, 14b are generally a half circle in shape (see FIGS. 6 and 9). The effective length EL of a needle 14a from suture 12 to tip 39 (the chord length) is approximately the diameter of a half circle. The effective width EW, i.e., measured at 90° to chord length at the middle of the chord is approximately ½ the diameter (the radius) of the half circle. Because the slits 32 may be disposed at an angle α relative to the length dimension L of the package 10, the needles 14a, 14b may be held with the effective length EL thereof approaching an orientation parallel to the length (L) dimension of the package (and the effective width approaching an orientation perpendicular to the length dimension (L) of the package. Since the effective width EW of the needles 14a, 14b is only half the effective length, the required number of needles 14a, 14b may be spaced horizontally and the pledgets interposed therebetween without exceeding an acceptable width dimension for the package 10, e.g., as related to the typical width of the grip span of the human hand. This economy of package width also preserves the option of utilizing existing packaging machinery and materials, e.g., those associated with overwrapping and packing the packages 10 into a carton. The slit 32 angle α may be varied from 0° (as shown in FIG. 1) to about 90°.

Figure 2:
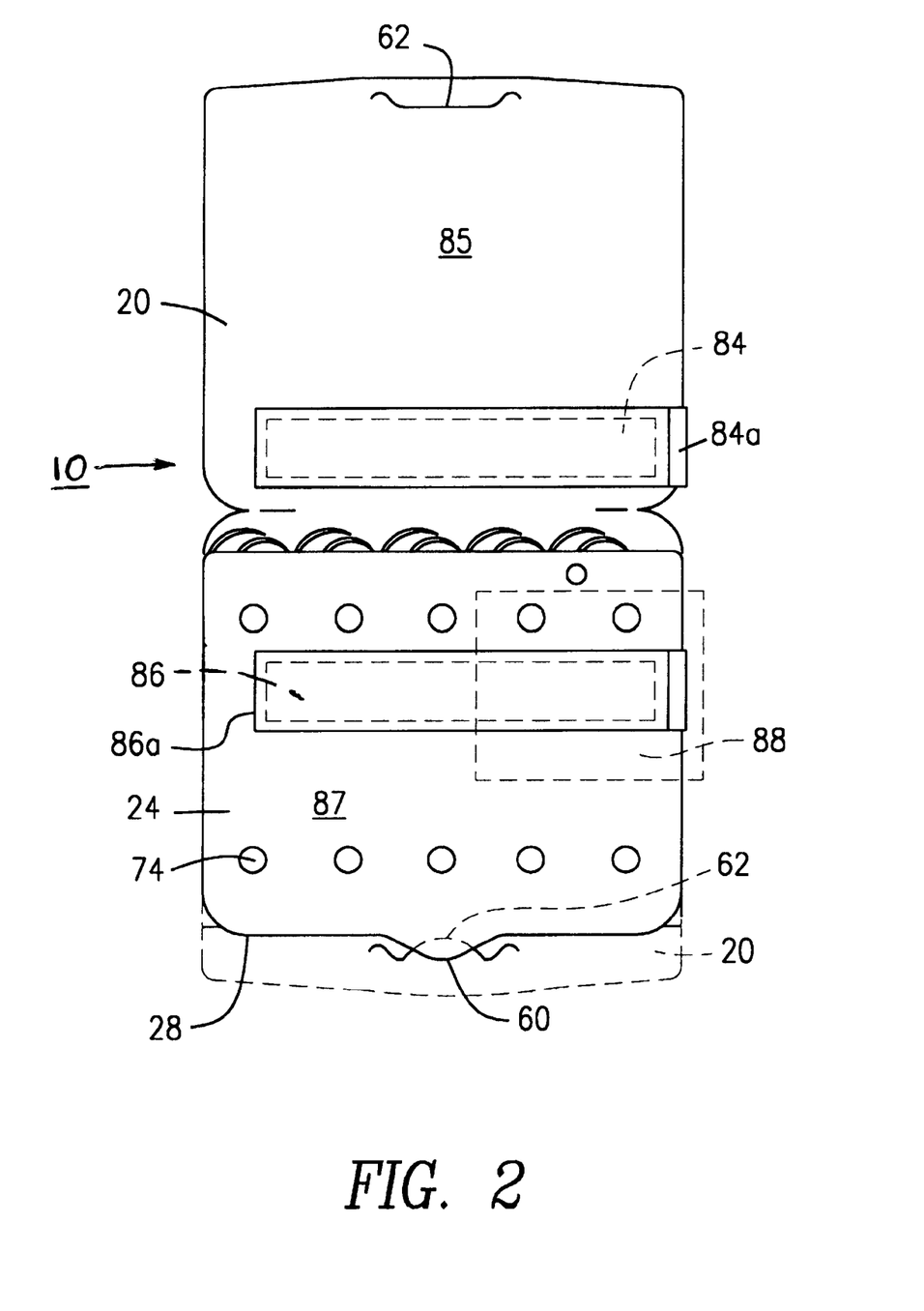
FIG. 2 is a plan view of the suture package of FIG. 1 in a partially folded state.
Figure 3:
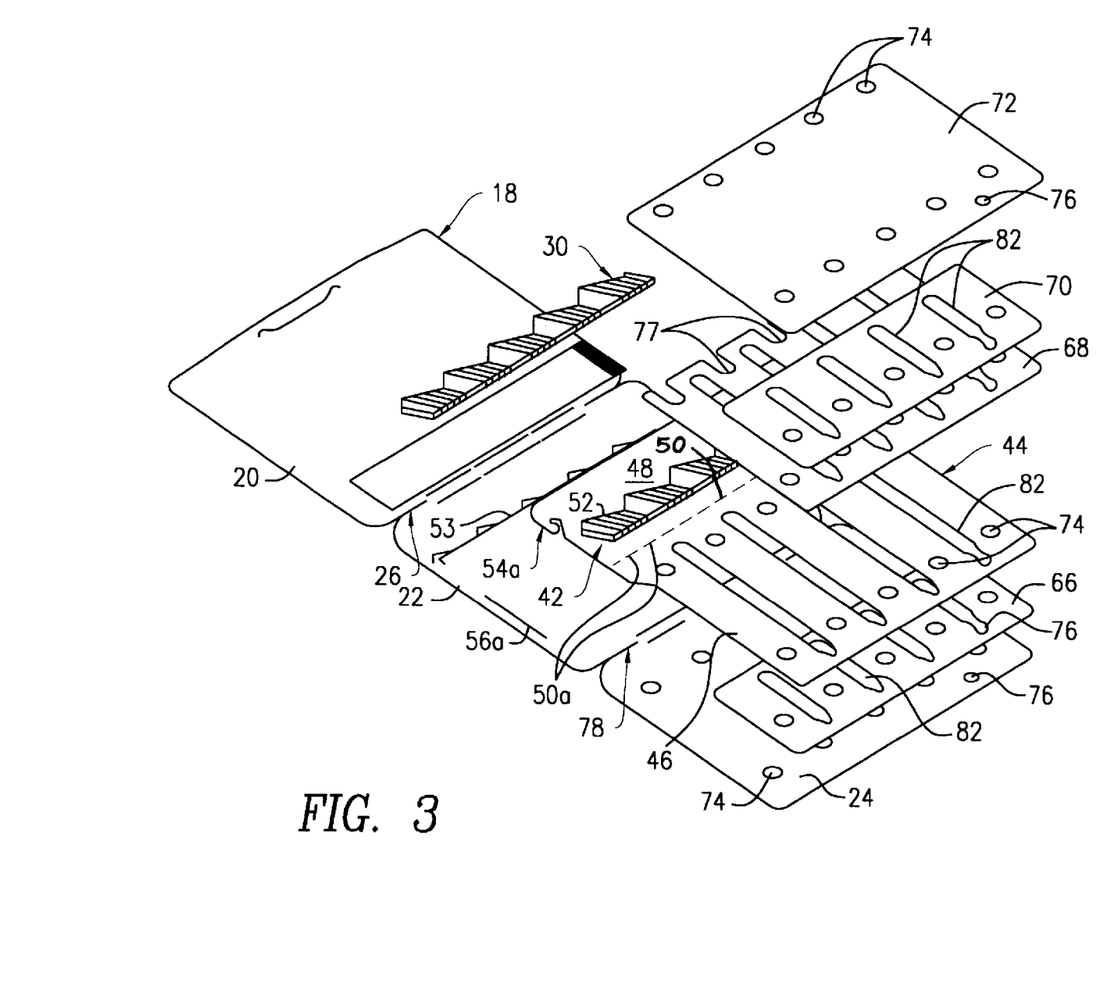
FIG. 3 is an exploded view of the suture package of FIGS. 1 and 2.

As shown in FIGS. 1 and 3, a second needle park 42 is affixed to an elongated divider panel 44. The divider panel 44 has a bottom portion 46 and a top portion 48 delimited by a fold line 50, which may be rendered more flexible by a plurality of perforations 50a. The top portion 48 and the subpanel 22 are preferably provided with printed guides 52, 53 indicating the proper position for the needle park 30, 42, respectively which may be coated on one side with a contact adhesive to be attached thereto. A pair of tabs 54a, 54b extend from the top portion 48 and are received in slots 56a, 56b provided in the middle subpanel 22. As can be appreciated from FIGS. 1 and 4, the middle subpanel 22 is the area where the needles 14a, 14b and pledgets 16 are parked, i.e., either on the main folder 18 or on the divider panel 44. The bottom subpanel 24 supports a multi-compartment pocket structure 58 that stores loops of suture 12 as described in U.S. Pat. No. 6,029,806. As shown in FIG. 2, the bottom subpanel 24 folds over the middle subpanel 22 covering the needles 14a, 14b and pledgets 16. The top subpanel 20 folds down over the folded bottom subpanel 24 to close the suture package 10 and is locked in that position by mating tab 60 and tab slot 62.

As shown in FIG. 1, the fold line 50 in elongated divider panel 44 is offset from the fold line 28 in main folder 18. More particularly, the fold line 50 is disposed closer to the pocket structure 58 than the fold line 28. Because the bottom portion 46 of the divider panel 44 is substantially fixed relative to the bottom subpanel 24 as explained more fully below, the offset fold lines 28, 50 require that the top portion 48 of the divider panel 44 articulates relative to the middle subpanel 22 when the bottom subpanel 24 is moved from the unfolded position (shown in FIG. 9) to the folded position (shown in FIG. 2, with FIG. 1 showing an intermediate position). It is preferable, however, to secure the top portion 48 in a position substantially parallel to the middle subpanel 22, such that the needle parks 30, 42 are substantially parallel, presenting an orderly array of two rows of needle pairs 14a, 14b, one row above the other. Furthermore, it is preferred that the top portion 48 be secured relative to the middle subpanel 22 to prevent the top portion 48 from flapping back and forth, such that the top portion 48 would have to be held in order to grasp a needle 14a, 14b from needle park 42. These functions are performed by the tabs 54a, 54b which insert into slots 56a, 56b. When the bottom subpanel 24 is folded up, the tabs 54a, 54b traverse the slots 56a, 56b, moving away from the lower end of the slots toward the upper end and permitting the top portion 48 to slide upward and in parallel relative to the middle subpanel 22. Hooks 64a, 64b (see FIG. 5) are provided at the tips of tabs 54a, 54b to retain same in slots 56a, 56b. As can be appreciated from FIG. 1, the sutures 12 attached to the needles 14a, 14b stored in the upper needle park 30 are spaced apart from each other and do not overlay those attached to the needles 14a, 14b stored in the lower needle park 42, nor vice versa. The divider panel 44 assures that all sutures 12 associated with needle park 42 are visually distinct from and may be grasped without inadvertently grasping a suture 12 associated with the upper needle park 30. As shown diagrammatically in FIG. 10, the offset fold line 50 preserves a spacing between the folded divider panel 44 and the folded main folder 18. In this manner, undesirable compression and sharp bending of the sutures 12 between the fold lines 50 and 28 are avoided.

The pocket structure 58 exhibits a plurality of individual pockets 58a, 58b, 58c, 58d and 58e. FIG. 3 shows that the pockets 58a–e may be divided into a plurality of stacked compartments (in the Z direction) by successive divider panels 66, 44, 68, 70 overlaid upon bottom subpanel 24 and covered by cover panel 72. All the divider panels 66, 44, 68, 70, as well as the subpanel 24 and cover panel 72 have winding pin apertures 74 to permit installation upon a suture winding jig (not shown, but fully described in U.S. Pat. No. 6,029,806). An alignment hole 76 may also be provided in each divider panel, e.g., 66, to assure proper orientation of the panels, e.g., 66, on the winding jig. More particularly, the divider panels, e.g., 66, have a predetermined preferred assembly orientation due to the position of winding pin apertures 74 and the specific surfaces coated by sealing compositions, e.g., polyethylene, that laminate successive dividers, e.g., 66, to form the pocket structure 58. The dividers, e.g., 68 may have other features such as reliefs 77 that dictate a particular assembly orientation. The reliefs 77 guide and hold a suture 12 passing from behind divider 68 to a position in front of divider 68. The depth of reliefs 77 may be used to control the length of suture 12 consumed in traversing the divider 68, as well as holding the suture 12 to prevent motion thereof along the top edge of the divider 68.

U.S. Pat. No. 6,029,806 is incorporated herein by reference for its teachings concerning the formation of a multi-compartment pocket structure 58 and the method of winding suture 12 on a winding jig to distribute the suture 12 through the compartments of the pockets 58a–e. For example, the U.S. Pat. No. 6,029,806 patent describes a serpentine winding method that progresses in the Z direction, i.e., upwards through each layer of the package. Divider panels (cover sheets) extend in the X and Y directions, with each suture loop resting on a divider panel, such that the suture loop also extends in the X and Y directions. Each suture may occupy a plurality of superimposed compartments in the pocket, with the suture extending in the Z direction as it traverses from the first compartment into the second compartment and with only one loop of suture in each compartment. The use of divider panels, e.g., 66, of different dimensions facilitates winding different length sutures in the X, Y and Z directions and having the suture 12 end in the desired location, e.g., such that the pledget 16 is visible or is in position to be parked in a needle park, e.g., 30.

The divider panels, e.g., 66 and cover panel 72 are constructed of any sheet material, including: paper, paperboard, plastic, TYVEK®, fabric, metal foil and/or laminates of same. Particularly preferred materials are paperboard such as five point to twelve point solid bleached sulfate board or twenty seven pounds per ream bleached Kraft paper. As noted below, one or more of the dividers, e.g., 66 and/or the cover sheet 72 may be at least partially coated with a heat sealing film, for example, a low density polyethylene or a polyvinylchloride.

After the sutures 12 are wound and the needles 14a, 14b and pledgets 16 parked, the pocket structure 58 is formed by applying a heat sealing die having the shape of the sealing lines 80 to the cover panel 72. The heat sealing die melts the heat sealing film on each of the cover panel 72 and the divider panels 66, 44, 68, 70, which causes them to adhere to each other and to the bottom subpanel 24 of the folder 18. Multi-compartment pockets 58a–e are thereby formed in the suture package 10, with each pocket, e.g., 58a potentially containing a plurality of sutures 12 arranged in superimposed compartments. Since paper is a thermal insulator, depending upon the number and thickness of dividers and the heat sealing film used, it may be required to perform sequential heat sealing of each successive divider panel, e.g., 66 to form the individual pockets 58a–e. The divider panels, e.g., 66 of the suture package 10 of the present invention have a plurality of seal vents 82 that permit the cover panel 72 to bond directly to the bottom subpanel 24, reducing the energy, time and steps required to bond a stack of divider panels, e.g., 66 without seal vents 82. More particularly, the side of the cover panel 72 facing the bottom subpanel 24 may be coated with a heat sealing film. When a heat sealing die is impressed upon the stacked divider panels 66, 44, 68, 70 each of which have aligned seal vents 82, the heat sealing film coated on the cover panel 72 is urged into contact with the bottom subpanel 24 through the seal vents 82. Upon melting and cooling, the cover panel 72 is thereby bonded to the bottom subpanel at the pocket seal lines 80. Since the seal vents 82 allow the cover panel 72 to bond directly to the bottom subpanel 24, the energy required to form the pocket seal lines 82 is greatly reduced, Similarly, there is no requirement for multiple, sequential sealing steps resulting in a greatly simplified, energy efficient and rapid fabrication process. Since only the cover panel 72 bonds to the bottom subpanel 24, only one surface, i.e., either the upper surface of the bottom subpanel 24 or the back of the cover panel 72 needs to be coated with sealing compound.

As shown in FIG. 2, the top subpanel 20 has a closure slot 62 which receives a mating lock tab 60 extending from the package 10 proximate fold line 28 when the top subpanel 20 is folded down over the folded bottom subpanel 24 to close the package 10. The closed position of the package 10 is shown in phantom in FIG. 2. Because the package 10 is a one piece bii-fold package with three subpanels 20,22, 24, there is no need for a separate sleeve to be slipped over the package 10 to close it. Accordingly, the present invention avoids the associated costs and handling associated with making, assembling and using a separate sleeve.

Sutures are available in different colors, e.g., white and green. In accordance with the present invention, a suture package 10 with multiple sutures 12 preferably utilizes sutures of at least two different colors arranged in a pattern that allows the scrub nurse to readily distinguish one suture from another. For example, in the embodiment described above in reference to FIGS. 1 through 3, ten double-armed sutures 12 are packaged in the suture package 10. The needle pairs 14a, 14b of the ten sutures 12 are arranged in two horizontal rows of five pairs each. An exemplary arrangement of associated suture colors would be, in the top row: white, and in the bottom row: green. Alternating white and green sutures 12 can be utilized. In this manner, the scrub nurse can readily associate the needle pairs 14a, 14b with the correct suture 12. By color coding the sutures 12 with contrasting colors, more sutures 12 can be stored in a package of a given size without causing confusion, and the two needles 14a, 14b of a suture 28 can be separated on the needle parks 30, 42 without loss of correlation, i.e., the ability to recognize that the two needles 14a, 14b are attached to the same suture 12. The needle parks 30, 42 assist in identification of the individual sutures 12 by separating the needles 14a, 14b of each suture horizontally and promoting rapid arming and release of needles. During surgery, the present invention preserves the rhythm between the scrub nurse and the surgeon as sutures are passed back and forth, with alternating green and white colored sutures aiding in identifying the two ends of a single suture and also helping the surgeon identify the suture ends to tie at the surgical site. The individual parking of needles 14a, 14b and pledgets 16, as well as the storage of sutures 12 in the multi-compartment pocket structure 58, prevents sutures from knotting on themselves, on adjacent sutures 12, on their own pledgets 16, or on adjacent pledgets 16. Each of these benefits preserves the rhythm between the surgeon and the scrub nurse, which shortens the duration of the surgery and promotes successful operations.

FIGS. 1 and 2 show mounting tapes 84, 86, e.g., in the form of double-sided tape covered by a substantially coextensive release sheet 84a, 86a or an adhesive area printed on the package 10 and covered by a release sheet 84a, 86a. The mounting tapes 84, 86 permit the suture package 10 to be adhered to a surface to facilitate holding the package 10 in a predetermined position to aid in dispensing the sutures 12. Mounting tape 84 is positioned on the interior surface 85 of top subpanel 20, such that the package 10 can be opened, the mounted tape 84 activated by removing the release sheet 84a and the subpanel 20 bent back to a position parallel to middle subpanel 22. The activated mounting tape 84 can then be applied to a selected surface to adhere the package 10 to the surface in an open position. Mounting tape 86 is positioned on the rear surface 87 of subpanel 24. In use, the mounting tape 86 may be activated by removing the release sheet 86a and then adhered to a surface, such as a Mayo stand. When used in conjunction with one another, mounting tapes 84 and 86 may be used to secure the package in an open position to a surface having any orientation, such as the vertical orientation. The mounting tapes 84, 86 are selectively activatable, such that they do not interfere with use of the package if surface mounting is not desired. As with the needle parks 30, 42, the positioning of the mounting tapes 84, 86 may be indicated to the assembler of the package 10 by guides printed on surfaces 85 and 87.

Figure 9:
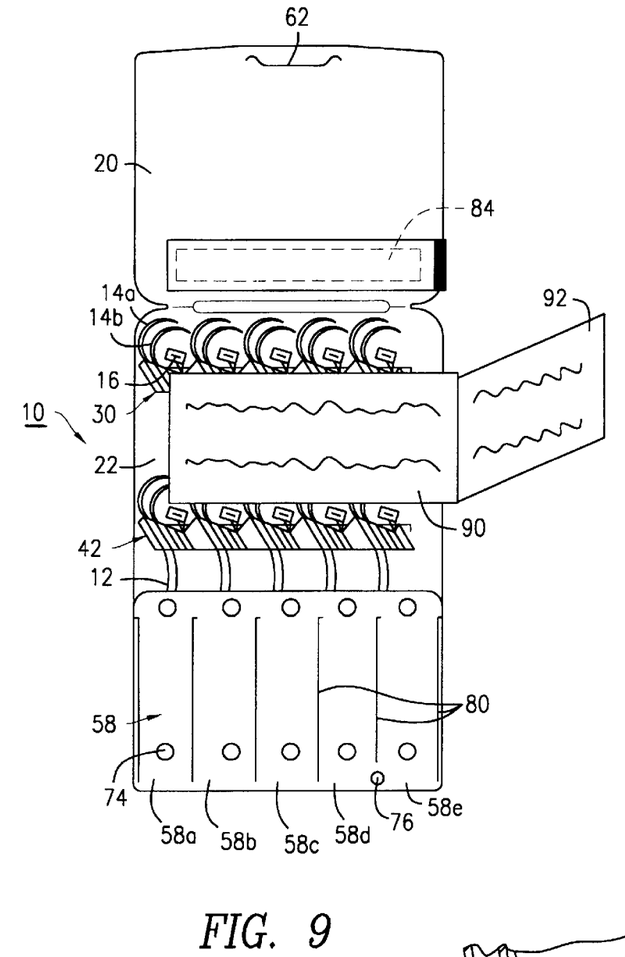
FIG. 9 is a plan view of a suture package of FIGS. 1–3 utilizing a message card.
Figure 10:
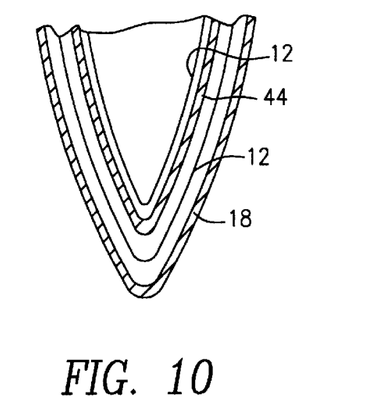
FIG. 10 is a diagrammatic depiction of a portion of the suture package of FIGS. 1–3 in a folded condition, as seen from the side.

FIGS. 2 and 9 show message carriers 88 (phantom view), 90 which can be utilized to convey information in the form of text or graphics (pictorial illustration). The information supplements the information provided elsewhere on the package 10 and may be in the form of a reminder or conveyor of special instructions, e.g., applicable to a method of use of the sutures 12 or a warning. The message carriers 88, 90 may convey information that is complementary or repeats information provided in a product information manual. The message carriers 88, 90 may be adhered resiliently or removably to the package 10, be mechanically coupled thereto, e.g., by folding around an edge of a subpanel, e.g., 24 (see FIG. 2) or merely placed in the package 10. Each message carrier 88, 90 may include an attention flag 92 in the form of a folded panel. The attention flag 92 is preferably biased away from a parallel orientation relative to the message carrier 90 such that when the package 10 is opened, the attention flag 92 sticks out to get the attention of the person opening the package 10. The attention flag 92 may be blank or contain information similar to and/or complementary to the message carriers 88, 90.

Figure 4:
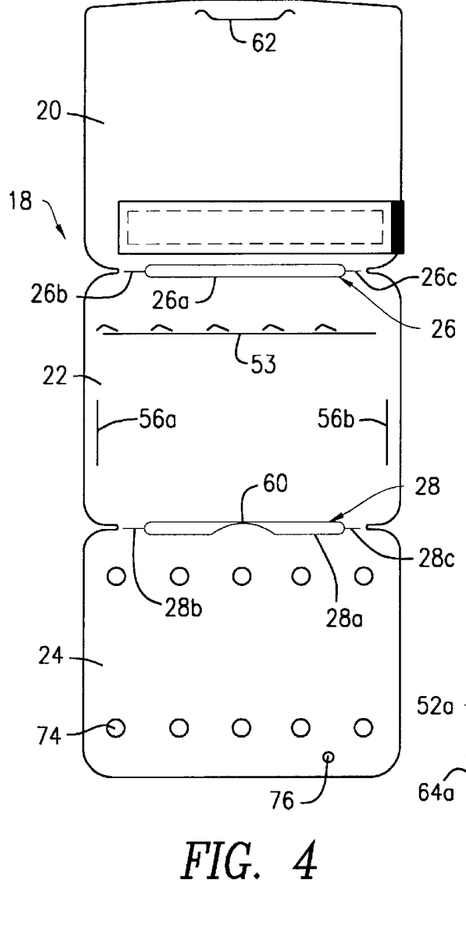
FIG. 4 is a plan view of a main folder of the suture package of FIGS. 1–3.

FIG. 4 shows the main folder 18 prior to the application of the needle park 30, divider panel 44 and pocket structure 58. The printed guide 53 for needle park 30 is visible in this view. The closure slot 62 and lock tab 60 are evident, as are the slots 56a, 56b that slidably accommodate the tabs 54a, 54b of the divider panel 44.

Figure 5:
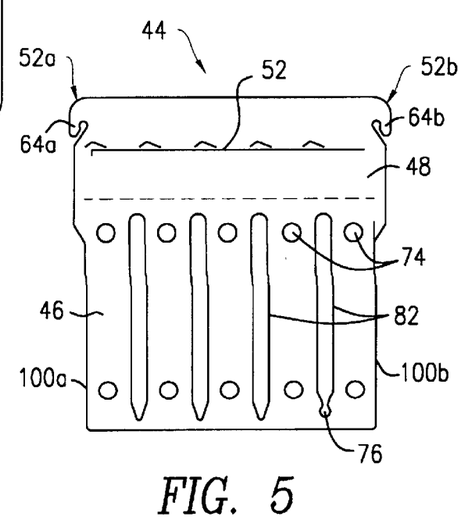
FIG. 5 is a plan view of a needle-retaining divider panel of the suture package of FIGS. 1–3.

FIG. 5 shows the divider panel 44 prior to incorporation into the pocket structure 58 or assembly to the main folder 18. As noted above, the top portion 48 of the divider panel 44 has a printed guide 52 to aid in placing needle park 42. Relieved opposing peripheral edges 100a, 100b on either side of the divider panel 44 like seal vents 82 permit the cover panel 72 to seal to the bottom subpanel 24 to form pockets 58a and 58e.

Figure 6:
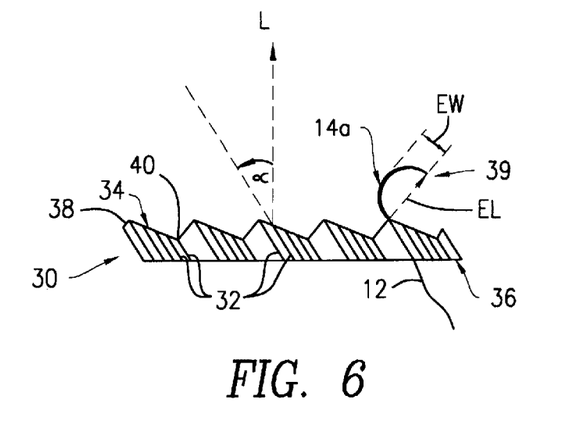
FIG. 6 is a plan view of a needle park used on the suture package of FIGS. 1–3.

FIG. 6 shows the needle park 30 with upper serrated edge 34, lower straight edge 36 and angled slits 32 at angle a as described above.

Figure 7:
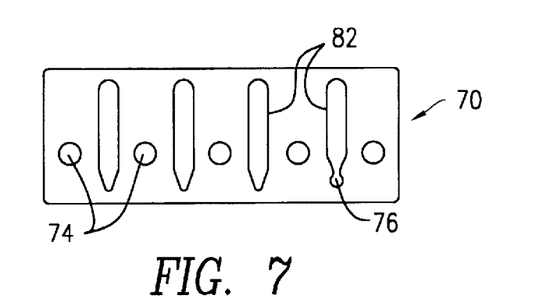
FIG. 7 is a plan view of a small-sized divider panel of the suture package of FIGS. 1–3.
Figure 8:
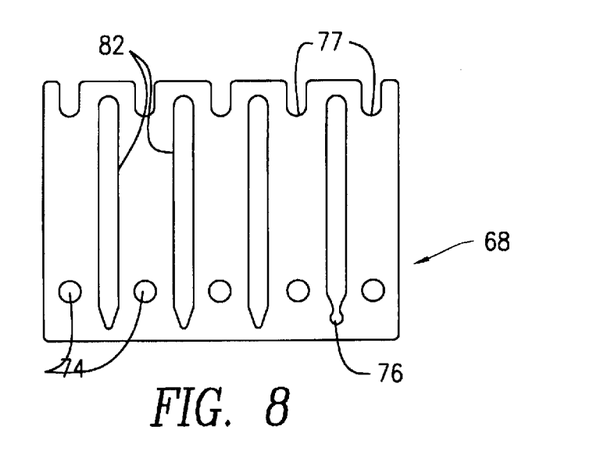
FIG. 8 is a plan view of a full-sized divider panel of the suture package of FIGS. 1–3.

FIGS. 7 and 8 show half divider panel 70 and full divider panel 68, respectively. The half divider panel 70 is dimensioned to "take up" less length of suture 12 such that the pledget 16 will park in the valley 40 of the needle park 30 or 42, as appropriate. Since different suture lengths may be stored in packages 10 with the same external dimensions, the half divider panel 70 may be dimensioned to "use up" as much suture as is needed for parking the pledget 16. Accordingly, the half divider panel 70 may or may not be one-half the length of a full divider panel 68. As noted above, the full divider panel 68 may be provided with suture reliefs 77 to retain suture 12 therein or to adjust the length of suture "taken up" by the panel 68. It should be appreciated that although divider panels 68, 70 and suture reliefs 77 with constant length dimensions from side to side of the panel 68, 70 are shown, varying length divider panels 68, 70 or varying depth suture reliefs 77 may be employed to store sutures of varying length in the same package 10.

The suture package 10 described above may be modified to contain any number of sutures, with the preferred range being between two and ten sutures per package. Packages 10 containing the correct number of sutures for a particular surgical procedure can be provided and such packages can, if desired, contain an assortment of needle sizes with each size prominently and individually marked adjacent to the needle parks 30, 42. The suture packages 10 are sterilized after fabrication by radiation, heat, ethylene oxide, or any other convenient and conventional method which is not incompatible with the package or suture materials. Sterile packages are hermetically sealed in an outer envelope wrap to preserve sterility.

The pledgets 16 employed in the preparation of the suture packages 10 of the present invention may be made of any biologically compatible, needle pierceable resilient material and of a variety of sizes. In general, rectangular pads about 3 mm by 6 mm by 1–2 mm thick are satisfactory for most surgical procedures. The pledgets 16 may be fabricated of fabric, felt, or any similar cushioning material. One preferred pledget material is a Teflon impregnated polyester felt. While the present invention has been described in terms of packaging sutures with pledgets, the same apparatus, techniques, and teachings can be applied in packaging sutures without pledgets. While the foregoing description has been directed to a suture package having two suture sets arranged in superimposed compartments, it is possible to construct a suture package according to the present invention that has only one set of sutures or more than two sets of sutures.

It will be understood that the embodiments described herein are merely exemplary and that a person skilled in the art may make many variations and modifications without departing from the spirit and scope of the present invention. For example, the foregoing description has explained the invention as a package for double armed sutures but the package could also be utilized for single armed sutures. All such variations and modifications are intended to be included within the scope of the invention as defined in the appended claims.

What is claimed:

1. A suture package, comprising:
   a base panel;
   a first needle park attached to a front surface of said base panel for holding a first needle, said first needle attached to a first suture;
   a pocket having a plurality of compartments disposed on said front surface of said base panel, a first of said plurality of compartments receiving said first suture;
   a second panel smaller than said base panel coupled to said base panel substantially parallel thereto with said first suture disposed between said second panel and said base panel;
   a second needle park attached to a front surface of said second panel for holding a second needle, said second needle attached to a second suture, a second of said plurality of compartments receiving said second suture, said base panel having a first fold line between said first needle park and said pocket and said second panel having a second fold line between said second needle park and said pocket, said first fold line and said second fold line permitting said package to be moved from an unfolded state to a folded state wherein said pocket is folded toward said first needle park and said second needle park.

2. The suture package of claim 1, wherein said pocket includes an outer cover panel coupled to said base panel, said second panel extending between said base panel and said cover panel dividing said pocket and forming at least a portion of said plurality of compartments, said first compartment positioned between said base panel and said second panel and said second compartment positioned between said second panel and said cover panel.

3. The suture package of claim 2, wherein said base panel has a third fold line above said first needle park and distal to said pocket, whereby said base panel is divided into a top portion extending between said third fold line and a top edge of said base panel, a middle portion extending between said third fold line and said first fold line and a bottom portion extending from said first fold line to a bottom edge of said base panel, said first needle park disposed on said middle portion and said pocket being disposed on said bottom portion, said top portion forming a cover for said bottom portion and said middle portion when said package is in said folded state, said package thereby assuming a bi-folded state.

4. The suture package of claim 3, wherein said second fold line divides said second panel into an upper portion and a lower portion and said second fold line is disposed at a different distance from said bottom edge than said first fold line, said upper portion being articulable relative to said base panel when said package is moved from the unfolded state to the folded state.

5. The suture package of claim 4, wherein said upper portion is slidably secured to said base panel such that said upper portion is maintained substantially parallel to said middle portion when said package is in the unfolded state and the folded state.

6. The suture package of claim 5, wherein said upper portion is slidably secured to said base panel by mating tabs disposed on one of said upper portion and said base panel and slots disposed on the other of said upper portion and said base panel.

7. The suture package of claim 6, wherein said tabs have hooks at a free end thereof for preventing said tabs from being withdrawn from said slots.

8. The suture package of claim 5, wherein said second fold line is spaced from said first fold line when said package is in the folded state and the bi-folded state to allow said first suture to pass between said base panel and said second panel proximate to said first fold line and said second fold line without being compressed.

9. The suture package of claim 8, wherein said first fold line and said third fold line are gusseted fold lines that space said top portion from said middle portion and said middle portion from said bottom portion when said package is in the bi-folded state.

10. The suture package of claim 2, wherein said first suture has a first opposing needle disposed at an end of said first suture distal to said first needle and said second suture has a second opposing needle disposed at an end of said second suture distal to said second needle, said first suture and said second suture being double armed sutures, said first needle park having a plurality of needle receptacles including a needle receptacle for each of said first needle and said first opposing needle and said second needle park having a plurality of needle receptacles, including a needle receptacle for each of said second needle and said second opposing needle, each of said plurality of needle receptacles in said first and second needle parks receiving needles at an end thereof connected to suture, leaving a pointed end thereof uncontained.

11. The suture package of claim 10, wherein said first and second needle parks have an upper serrated edge with peaks and valleys, said plurality of needle receptacles each disposed proximate to one of said peaks, the pointed end of needles received therein extending toward one of said valleys.

12. The suture package of claim 11, wherein said plurality of needle receptacles in each of said first and second needle parks is oriented at an acute angle relative to the length of said suture package, the length being measured generally parallel to the direction traversed by suture from said first needle park to said pocket.

13. The suture package of claim 12, wherein said first and second sutures have pledgets mounted thereon and wherein said plurality of needle receptacles are a plurality of slits extending at least partially through said first and second needle parks and wherein a plurality of said slits are provided in said first and second needle parks for receiving said first and second sutures proximate said pledgets, said pledgets receivable within said valleys of said first and second needle parks proximate to the needles attached to said first and second sutures.

14. The suture package of claim 3, further including a first mounting tape attached to said top portion and a second mounting tape attached to said bottom portion, said first and second mounting tapes having an adhesive for adhering said package to a surface.

15. The suture package of claim 2, wherein said first needle park is disposed on said base panel above an upper edge of said second panel, said first suture extending from said first needle in said first needle park over said base panel and behind said second panel, said first suture having a first visible portion visible to a user from said first needle park to said upper edge of said second panel when said package is in the unfolded state, said second suture extending from said second needle in said second needle park over said second panel into said second compartment, said second suture having a second visible portion visible to a user from said second needle park to said second compartment, said second visible portion of said second suture longitudinally displaced from and readily visually distinguishable from said first visible portion of said first suture.

16. The suture package of claim 2, wherein at least one of said cover panel and said base panel has a heat sealing coating applied to at least a portion of a surface thereof, said heat sealing compound coupling said cover panel to said base and wherein said second panel has a plurality of vents therein permitting said cover panel to contact said base panel to couple thereto.

17. The suture package of claim 16, further including at least one additional divider panel disposed in at least one of said first compartment and said second compartment to form sub-compartments therein, said divider panel having a plurality of vents therein permitting said cover panel to contact said base to couple thereto.

18. The suture package of claim 1, further including a message carrier disposed within said package when said package is in a closed state, said message carrier bearing information for a user of said suture package.

19. The suture package of claim 18, wherein said message carrier has a fold line and is folded along said fold line when disposed within said suture package, said message carrier being self-biasing to an unfolded position, such that when said suture package is opened said message carrier assumes an unfolded position to gain the attention of the user.

20. A suture package for holding a plurality of double armed sutures having needles at both ends, comprising:
   a base panel;
   a needle park attached to a front surface of said base panel;
   a pocket having a plurality of compartments disposed on said front surface of said base panel for receiving sutures therein;
   said needle park having a plurality of needle receptacles including a needle receptacle for each of the needles on the plurality of double armed sutures, said needle receptacles receiving needles at an end thereof connected to suture, leaving a pointed end of the needles uncontained, said needle park having an upper serrated edge with peaks and valleys, said plurality of needle receptacles each disposed proximate to one of said peaks, said pointed end of received needles extending toward one of said valleys.

21. The suture package of claim 20, wherein said plurality of needle receptacles are oriented at an acute angle relative to the length of said suture package, the length being measured generally parallel to the direction traversed by suture from said needle park to said pocket.

22. The suture package of claim 21, wherein said sutures have pledgets mounted thereon and wherein said plurality of needle receptacles are a plurality of slits extending at least partially through said needle park and wherein a plurality of said slits are provided in said needle park for receiving suture proximate said pledgets, said pledgets receivable within said valleys of said needle park proximate to the needles attached to the suture.

23. A suture package for holding a plurality of double armed sutures having needles at both ends, comprising:
   a base panel;
   a needle park attached to a front surface of said base panel;
   a pocket structure with an exterior cover panel attached to said base panel at a plurality of points to form a plurality of individual pockets positioned side-by-side, a divider panel disposed between and extending parallel to said cover panel and said base panel, said divider panel dividing each of said individual pockets into a plurality of compartments for receiving suture therein, said divider panel having a plurality of vents therein through which said cover panel contacts said base panel and is adhered thereto by heat sealing compound.

\* \* \* \* \*

UNITED STATES PATENT AND TRADEMARK OFFICE
CERTIFICATE OF CORRECTION

PATENT NO.     : 6,739,450 B2
DATED          : May 25, 2004
INVENTOR(S)    : Roshdy, Constance E. and Porras, Elizabeth It is certified that error appears in the above-identified patent and that said Letters Patent is hereby corrected as shown below:

<u>Title page,</u>
Item [75], Inventors, "South Round Brook" should read -- South Bound Brook --

Signed and Sealed this

Twentieth Day of July, 2004

JON W. DUDAS
*Acting Director of the United States Patent and Trademark Office*